US00PP30414P2

(12) United States Plant Patent
Merz

(10) Patent No.: US PP30,414 P2
(45) Date of Patent: Apr. 16, 2019

(54) ***LIRIOPE* PLANT NAMED 'FAN DANCER'**

(50) Latin Name: *Liriope muscari*
Varietal Denomination: Fan Dancer

(71) Applicant: Michael Merz, Offenbach am Main (DE)

(72) Inventor: Michael Merz, Offenbach am Main (DE)

( * ) Notice: Subject to any disclaimer, the term of this patent is extended or adjusted under 35 U.S.C. 154(b) by 0 days.

(21) Appl. No.: 15/732,963

(22) Filed: Jan. 18, 2018

(51) Int. Cl.
*A01H 5/02* (2018.01)

(52) U.S. Cl.
USPC ..... Plt./450

(58) Field of Classification Search
USPC ..... Plt./450
See application file for complete search history.

*Primary Examiner* — Annette H Para

(57) ABSTRACT

A new cultivar of *Liriope* plant named 'Fan Dancer' that is characterized by violet flower buds and flowers borne on terminal fasciated racemes that become wider toward the tip and variegated green leaves with yellow-green stripes.

1 Drawing Sheet

Botanical classification: *Liriope muscari*.
Variety denomination: 'Fan Dancer'.

BACKGROUND OF THE INVENTION

The present invention relates to a new and distinct cultivar of *Liriope* plant botanically known as *Liriope muscari* and hereinafter referred to by the cultivar name 'Fan Dancer'.

The new *Liriope* is a naturally-occurring whole plant mutation of *Liriope muscari* 'Gold Band' (not patented). The new *Liriope* was discovered and selected by the Inventor as a single plant from within a population of plants of the parent in a controlled greenhouse environment in a cultivated area of Offenbach, Germany in 2012.

Asexual reproduction of the new cultivar 'Fan Dancer' first occurred by division in 2013 in Offenbach, Germany. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Liriope* cultivar 'Fan Dancer'. These traits in combination distinguish 'Fan Dancer' as a new and distinct cultivar apart from other existing known varieties of *Liriope*.

1. *Liriope* 'Fan Dancer' exhibits flower buds and flowers borne on terminal fasciated racemes that become wider toward the tip.
2. *Liriope* 'Fan Dancer' exhibits violet flower buds and flowers.
3. *Liriope* 'Fan Dancer' exhibits variegated green leaves with yellow-green stripes.

The closest comparison cultivars are *Liriope* 'Moneymaker' (not patented) and the parent plant *Liriope* 'Gold Band'.

'Fan Dancer' is distinguishable from 'Moneymaker' by the following characteristics:

1. *Liriope* 'Fan Dancer' exhibits flower buds and flowers borne on terminal fasciated racemes that become wider toward the tip. In comparison, the racemes of 'Moneymaker' are cylindrical and not fasciated.
2. *Liriope* 'Fan Dancer' exhibits variegated green leaves with yellow-green stripes. In comparison, the leaves of 'Moneymaker' are solid green.

'Fan Dancer' is distinguishable from the parent plant 'Gold Band' by the following characteristics:

1. *Liriope* 'Fan Dancer' exhibits flower buds and flowers borne on terminal fasciated racemes that become wider toward the tip. In comparison, the racemes of 'Gold Band' are cylindrical and not fasciated.
2. *Liriope* 'Fan Dancer' exhibits a larger number of flower buds and flowers than the number of flower buds and flowers of 'Gold Band'.

BRIEF DESCRIPTION OF THE DRAWING

The accompanying photograph illustrates the distinguishing traits of *Liriope* 'Fan Dancer'. The plant in the photograph shows an overall view of a 2 year old plant.

The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Liriope* cultivar named 'Fan Dancer'. Data was collected in Mainz, Germany from 2 year old greenhouse grown plants in 14 cm. diameter containers. The time of year was Fall and the temperature range was 20-28 degrees Centigrade during the day and 15-20 degrees Centigrade at night. No growth retardants were used. Color determinations are in accordance with The Royal Horticultural Society Colour Chart 2007 edition, except where general color terms of ordinary dictionary significance are used. The growing requirements are similar to the species. 'Fan Dancer' has not been tested under all possible conditions and phenotypic differences may be observed with variations in environmental, climatic, and cultural conditions, however, without any variance in genotype.

Botanical classification: *Liriope muscari* 'Fan Dancer'.
Annual or perennial: Perennial.
Parentage: 'Fan Dancer' is a naturally occurring whole plant mutation of *Liriope* 'Gold Band'.
Vigor: Moderate.
Growth habit: Clumping habit with curved foliage.
Plant shape: Upright with outwardly arching foliage.
Suitable container size: 20 cm.
Height: Average 33 cm. in height.
Diameter: Average 43 cm. in diameter.
Low temperature tolerance: −20° Centigrade.
High temperature tolerance: 40° Centigrade.
Propagation: Division.
Time to initiate roots in summer: 20 days to initiate roots at 25° Centigrade.
Time to initiate roots in winter: 30 days to initiate roots at 8° Centigrade.
Time to produce a rooted cutting or liner in summer: 20 days at 25° Centigrade.
Time to produce a rooted cutting or liner in winter: 30 days at 8° Centigrade.
Crop time: Approximately 1 year.
Root system: Thick and fleshy.
Root color: 145D.
Foliage:
*Leaf arrangement*.—Basal leaves, sessile.
*Leaf shape*.—Linear.
*Leaf apex*.—Acute.
*Leaf base*.—Truncate.
*Leaf dimensions*.—28 cm. in length and 14 mm. in width.
*Texture*.—Glabrous on both surfaces.
*Pubescence*.—None.
*Leaf margin*.—Entire.
*Venation pattern*.—Parallel.
*Young leaf color* (*upper surface*).—N137B with stripes 151B.
*Young leaf color* (*lower surface*).—137B with stripes N144A.
*Mature leaf color* (*upper surface*).—N137A with stripes 138B.
*Mature leaf color* (*lower surface*).—137B with stripes 138B.
*Vein color* (*upper surface*).—N137A.
*Vein color* (*under surface*).—137B.
*Durability of foliage to stress*.—High.
Flower:
*Inflorescence arrangement*.—Terminal fasciated racemes.
*Inflorescence dimensions*.—13 cm. in height, 5 mm. in width at base and 42 mm. in width at tip.
*Quantity of flowers and buds per inflorescence*.—Average 400.
*Quantity of flowers and buds per plant*.—Average 4000.
*Natural flowering season*.—August to October.
*Fragrance*.—None.
*Flowering habit*.—95% of flower buds do not open and remain closed.
*Flower bud dimensions*.—3 mm. in length and 2 mm. in diameter.
*Flower bud shape*.—Ovate.
*Bud color*.—N87B.
*Flower aspect*.—Outward.
*Flower shape*.—Campanulate.
*Flower dimensions*.—2 mm. in diameter and 3 mm. in height.
*Flower longevity*.—5 to 6 weeks.
*Number of petals*.—6.
*Fused or unfused*.—Fused.
*Petal arrangement*.—Base fused, flaring outward.
*Petal shape*.—Ovate.
*Petal texture*.—Smooth on both surfaces.
*Petal margin*.—Entire.
*Petal apex*.—Rounded.
*Petal base*.—Fused.
*Petal length*.—3 mm.
*Petal width*.—1 mm.
*Petal color when opening* (*upper side*).—86B.
*Petal color when opening* (*under side*).—86B.
*Petal color fully opened* (*upper side*).—N87B.
*Petal color fully opened* (*under side*).—N87B.
*Petal color fading to*.—N87B.
*Self-cleaning or persistent*.—Self-cleaning.
Peduncle:
*Peduncle dimensions*.—21 cm. in length and 5 mm. in diameter.
*Peduncle angle*.—0 degrees (vertical).
*Peduncle strength*.—Strong.
*Peduncle color*.—N80B.
Pedicels:
*Pedicel dimensions*.—1 mm. in length and 0.2 mm. in diameter.
*Pedicel angle*.—120 degrees.
*Pedicel strength*.—Strong.
*Pedicel color*.—N80B.
Reproduction organs:
*Stamen number*.—6.
*Anther shape*.—Oval.
*Anther size*.—0.5 mm. in length and 1 mm. in width.
*Anther color*.—18B.
*Amount of pollen*.—Moderate.
*Pollen color*.—18B.
*Pistil number*.—One.
*Pistil length*.—1.0 mm.
*Stigma shape*.—Club shaped.
*Stigma color*.—N80B.
*Style length*.—0.5 mm.
*Style color*.—N80B.
*Ovary color*.—N80B.
Fruit and seed: Fruit and seed production has not been observed to date.
Disease and pest resistance: Disease and pest resistance has not been observed to date.

The invention claimed is:

1. A new and distinct variety of *Liriope* plant named 'Fan Dancer' as described and illustrated.

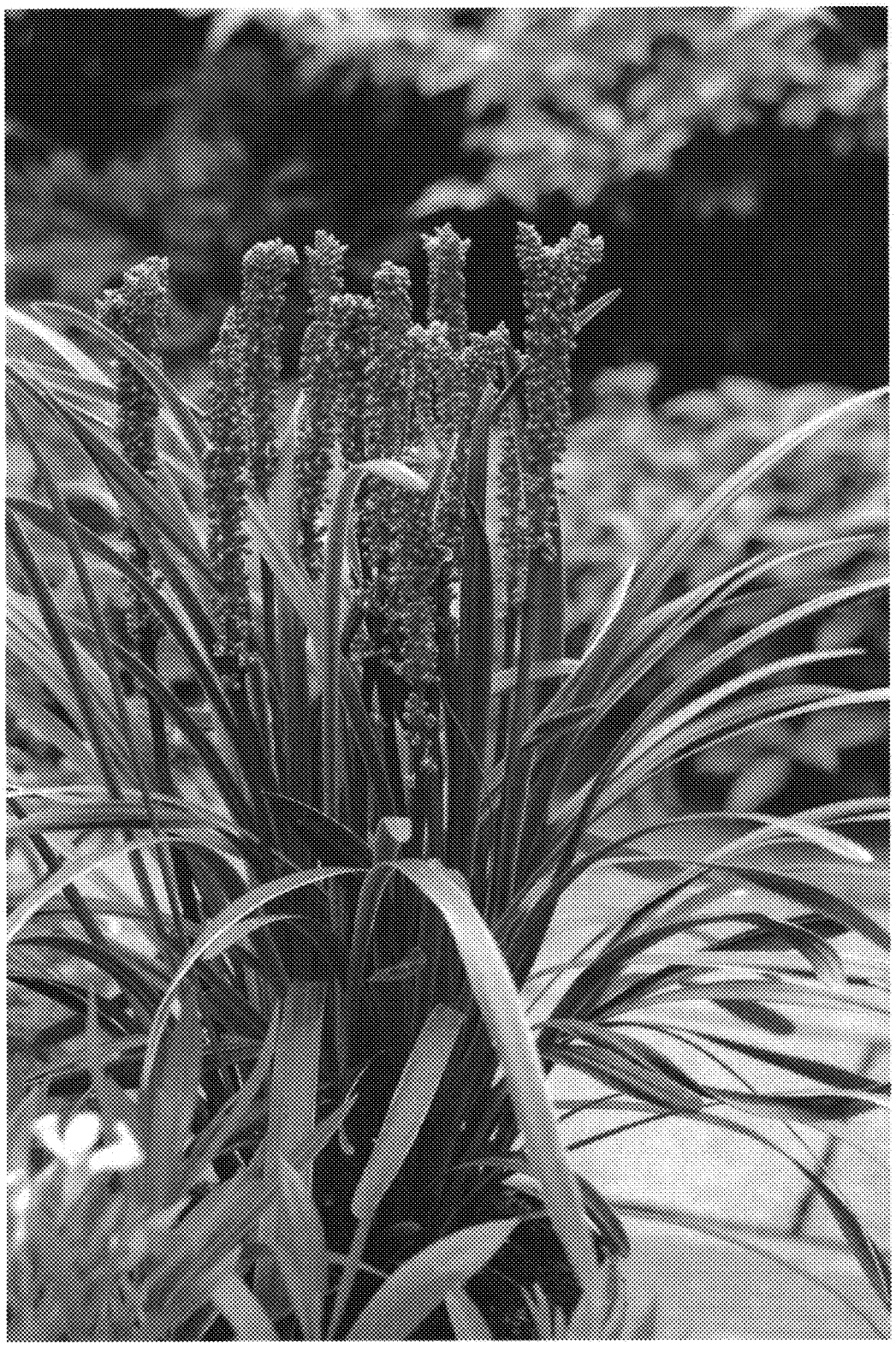

* * * * *